United States Patent [19]
Baldwin et al.

[11] Patent Number: 4,548,994
[45] Date of Patent: Oct. 22, 1985

[54] ISOLATION OF BACTERIAL LUCIFERASE

[75] Inventors: Thomas O. Baldwin; Thomas F. Holzman, both of Bryan, Tex.

[73] Assignee: The Upjohn Company, Kalamazoo, Mich.

[21] Appl. No.: 529,245

[22] Filed: Sep. 6, 1983

Related U.S. Application Data

[60] Division of Ser. No. 326,244, Dec. 3, 1981, Pat. No. 4,412,001, which is a continuation-in-part of Ser. No. 230,178, Jan. 30, 1981, abandoned.

[51] Int. Cl.[4] ............................................. C08F 8/30
[52] U.S. Cl. ............................ 525/329.9; 525/330.5; 525/331.3; 525/333.6
[58] Field of Search ............... 525/329.9, 330.5, 331.3, 525/333.6

[56] References Cited

U.S. PATENT DOCUMENTS

| 3,639,353 | 2/1972 | Brown | 525/329.9 |
| 4,064,110 | 12/1977 | Arlt | 525/329.9 |
| 4,076,917 | 2/1978 | Swift | 525/329.9 |
| 4,079,030 | 3/1978 | Takanen | 525/330.5 |
| 4,243,776 | 1/1981 | Marconi | 525/330.5 |

Primary Examiner—Paul R. Michl
Attorney, Agent, or Firm—L. Ruth Hattan

[57] ABSTRACT

The present invention provides a novel means for the isolation of bacterial luciferase and a novel affinity resin useful in said isolation.

12 Claims, No Drawings

ISOLATION OF BACTERIAL LUCIFERASE

This is a division of application Ser. No. 326,244, filed Dec. 3, 1981, now U.S. Pat. No. 4,412,001, which is a continuation-in-part of application Ser. No. 230,178, filed Jan. 30, 1981, now abandoned.

BACKGROUND OF THE INVENTION

The generally practiced method for the isolation of bacterial luciferase involving batch adsorption technique is described by J. Woodland Hastings, et.al., in Methods in Enzymology, Vol, LVII, 135 (1978) and A. Gunsalus-Miguel, et.al., J. Biol. Chem. 247(2), 398–404 (1972). Isolation of bacterial luciferase by affinity chromatography using immobilized flavin mononucleotide to bind the enzyme is described by C. A. Waters, et. al., in Biochem. Biophys. Res. Comm. 57, No. 4, 1152 (1974). Neither of these methods is particularly efficient in that each involves a considerable amount of time to perform and/or low yields of enzyme are recovered.

The method of isolating bacterial luciferase as described herein not only reduces significantly the amount of time required to isolate the enzyme, but also results in high yields of relatively pure enzyme.

SUMMARY OF THE INVENTION

One embodiment of the present invention is a method for isolating of purifying bacterial luciferase which comprises suspending the sample containing the enzyme to be isolated in an anionic buffer, contacting said suspended sample with an affinity resin, described below, washing the mixture with the anionic buffer followed by application of a cationic buffer to release the enzyme which may then be isolated.

Another embodiment of the present invention is a novel affinity resin which comprises a support material to which is attached a spacer arm which in turn is attached to a ligand which specifically binds the bacterial luciferase. Schematically the affinity resin may be represented as follows:

support material~spacer~ligand      Formula I

Suitable support material which may also be referred to as gel beads or resins, are any polysaccharide base matrix, such as sepharose, sephadex, cellulose; or, an acrylamide base or polyacrylamide which also may be cross-linked with a sepharose or sephadex or a polyacrylonitrile base such as the particulate support material described in U.S. Pat. No. 4,143,203; or, nylon surfaces, such as, nylon fibers or mesh; or, glass surfaces, such as, glass beads and in particular controlled-pore glass (CPG) as described by H. H. Weetall and A. M. Filbert, Meth. Enzymol. 34, 59–72 (1974).

The spacer arm is incorporated into the affinity resin by reaction of the support material with any of a variety of conventional difunctional compounds such as alkylenediamines, aliphatic aminoacids or a diglycidyl ether, and the ligand is a compound which binds to bacterial luciferase.

DETAILED DESCRIPTION OF THE INVENTION

Suitable support material for use in preparing the affinity resin of the present invention bear groups which will react with the difunctional compound utilized to incorporate the spacer arm into the affinity resin or are capable of being rendered reactive to said compounds.

Suitable reactive groups which may be present on the support material include carboxy, hydroxy, sulfhydryl, amino, epoxy or carboxysuccinimide groups. It is important that the support material not interact with the protein being isolated, i.e., the bacterial luciferase. When nylon is employed as the support material it is treated, for example, with N,N-dimethyl-1,3-diaminopropane by the general procedure described by W. E. Hornby, et. al., FEBS Letters 23, 114 (1972). Succinimide derivitization of resins bearing carboxy groups may be accomplished by treatment with N-hydroxylated succinimide using carbodiimide activation. When CPG is the support material the functional OH is a silanol which is treated with an organosilane such as epoxysilane, sulfhydrylsilane, alkyl-$C_{1-4}$-amine silane or an alkyl $C_{1-4}$-halosilane such as alkylchlorosilane by generally known procedures; see H. H. Weetall and A. M. Filbert, ibid.

As a matter of convenience the affinity resin of the present invention is represented schematically as in Formula I and the manner of constructing or preparing the affinity resin is set forth in terms of beginning with a support material and reacting it with a difunctional compound to give a support material~spacer arm unit which in turn is reacted with the ligand. However, it will be readily apparent that the affinity resin may be constructed by reacting the ligand with the difunctional compound to give a spacer arm~ligand unit which in turn is reacted with the support material. Also commercially available resins or coupling gels having the spacer arm already attached, such as, AH-Sepharose 4B and CH-Sepharose 4B, may be utilized in preparing the affinity resin of the present invention.

Difunctional compounds which are used to provide the spacer arm moiety of the affinity resins of the present invention are represented by the following Formulas II and III:

$NH_2$—Q—R      Formula II

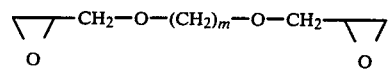      Formula III

In Formula II, Q is a straight or branched alkylene moiety having from 2 to 8 carbon atoms, and R is amino, carboxy or carboxysuccinimide. In Formula III, m is an integer from 2 to 6.

Carboxysuccinimide is taken to mean the group:

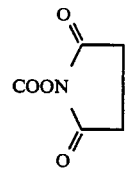

In Formula II it is preferred that Q is a straight chain alkylene moiety, i.e., —$(CH_2)$—$_{2-8}$ although branching of 1 or 2 carbons is suitable for the present invention. The compounds of Formulas II and III are commercially available or can be prepared by procedures well known in the art. Illustrative examples of compounds of Formula II are ethylenediamine, 1,3-propylenediamine, 1,6-hexamethylenediamine, 1,3-isobutylenediamine, 1,4-butylenediamine, glycine, β-alanine, alanine, α-aminopropionic acid, γ-aminopropionic acid, γ-aminobutyric acid, γ-aminohexanoic acid and of course the corresponding carboxysuccinimide derivatives thereof obtained via reaction with N-hydroxysuccinimide. Illustrative examples of compounds of Formula III are 1,4-bis(2,3-epoxypropoxy)butane, 1,2-bis(2,3-epoxypropoxy)ethane, and 1,6-bis(2,3-epoxypropoxy)hexane.

The ligand portion of Formula I are compounds which have a specific affinity for bacterial luciferase. In addition to 2-(2,4-dichloro-6-phenylphenoxy)ethylamine and 2-(2,3-dichloro-6-phenylphenoxy)ethylamine typically the ligands employed in the present invention are diphenylalkylene or ortho-, meta- or para-biphenylylalkylene containing compounds of the following Formula IV.

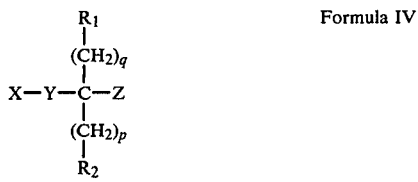

Formula IV wherein X is —COOH, —COhalogen, halogen, OH, SH, $NH_2$ or epoxy, i.e.,

Y is a bond or an alkylene chain of 1 to 4 carbon atoms, one or two carbon atoms of which may be branched; Z is hydrogen or a straight or branched alkyl group having from 1 to 4 carbon atoms; q is zero or one; p is zero, one or two; $R_1$ is hydrogen, phenyl or phenyl substituted with one or two substituents selected from halogen, trihalomethyl, e.g., trifluoromethyl, a straight or branched alkoxy group having from 1 to 4 carbon atoms or a straight or branched alkyl group having from 1 to 4 carbon atoms; and $R_2$ is ortho-, meta-, or para-biphenylyl, phenyl, or phenyl substituted with one or two substituents selected from halogen, trihalomethyl, e.g., trifluoromethyl, a straight or branched alkoxy group having from 1 to 4 carbon atoms or a straight or branched alkyl group having from 1 to 4 carbon atoms with the provisos that: (a) when $R_2$ is biphenylyl each of p and q is zero and $R_1$ is hydrogen; (b) when p is two, q is zero; and (c) when $R_2$ is other than biphenylyl, $R_1$ is other than hydrogen.

As used herein halo and halogen means chloro, fluoro, bromo and iodo. Preferred halogens are chloro and bromo.

Illustrative examples of alkylene groups which Y represents are ethylene, 1,3-propylene, 1,2-isopropylene and 1,4-butylene.

Illustrative examples of alkyl groups which Z represents or which may be present as substituents on the phenyl rings represented by $R_1$ and $R_2$ are methyl, ethyl, n-propyl, isopropyl and n-butyl.

Illustrative examples of alkoxy groups which may be present on the phenyl rings represented by $R_1$ and $R_2$ are methoxy, ethoxy, and n-propoxy.

Ligands of Formula IV wherein X is COOH, COhalogen and $NH_2$ are preferred. Ligands of Formula IV wherein $R_1$ and $R_2$ are phenyl or wherein Z is hydrogen, methyl or ethyl are also preferred. The most preferred ligands of Formula IV are 2,2-diphenylpropylamine, 1,1-diphenylpropylamine, 3,3-diphenylpropylamine, 2,2-diphenylpropionic acid and 3,3-diphenylpropionic acid.

When Y in Formula IV contains at least three carbon atoms in a straight chain relationship, i.e., Y is 1,3-propylene or 1,3-isobutylene, the ligand may be attached directly to the support material bypassing the use of a spacer arm to give an affinity resin which may be depicted schematically as support material~ligand       Formula V wherein support material and ligand are as defined hereinabove except Y contains at least 3 straight chain carbon atoms.

It should be recognized that as the term ligand is used in reference to affinity resin the terminal functional group represented by X in Formula IV has been reacted with the functional group carried on the support material in the case of affinity resins of Formula V or with the distal end, i.e., end furthest from the support material, of the spacer arm in the case of affinity resins of Formula I.

The compounds of Formulas I and II are reacted with suitable support materials by procedures well known in the art. In preparing the affinity resin of Formula I, the reaction of appropriate support materials as described hereinbelow with the compounds of Formulas II and III as described above will result in support material-spacer arm units having the general structures depicted in Formulas A to F set forth in Chart A. In Formulas A to F, O~ represents the support material; the groups R and Q have the meanings defined in Formula II; m has the meaning defined in Formula III; $R_3$ is oxygen or sulfur; and $R_4$ is oxygen, sulfur or —NH—. Illustratively, support materials bearing hydroxyl or sulfhydryl groups are allowed to react with compounds of Formula II by the procedures described by J. Porath, Nature 218, 834 (1968) and J. Porath, et. al., J. Chromatogr. 86, 53 (1973) whereby cyanogen bromide is suspended in an aqueous alkaline solution, e.g., 0.1M sodium bicarbonate, having a pH of 12, to which is added the support material, such as agarose, at a ratio of 2 ml of cyanogen bromide solution per each ml of resin suspended in 0.1M aqueous sodium bicarbonate. The mixture is incubated about ten minutes with gentle stirring at room temperature, vacuum filtered then washed with several volumes of cold distilled water to neutrality to give activated support material suitable for coupling with compounds of Formula II.

A compound of Formula II is added to a 0.2M aqueous sodium bicarbonate buffer (pH 9) at a concentration of 5 to 50 mg of compound per ml of buffer. The buffer solution is added to a sufficient quantity of the activated support material described above to give a 1:2 dilution of compound to resin, and the mixture is incubated at 4° C. for 12 to 24 hours. See Formula A of Chart A.

In coupling the above-described hydroxy containing resin or gel, i.e., support material with a compound of Formula III, the support material need not be activated and is suspended in 0.6M aqueous sodium hydroxide containing 2 mg of sodium borohydride per ml of solution. Equal volumes of the thus suspended resin and a compound of Formula III are reacted at room temperature (about 25° C.) with gentle stirring for 12 to 24 hours then washed with distilled water to pH 7. See Formula B wherein $R_4$ is oxygen or sulfur. Note that the —OH may be in the penultimate position with the attachment to the terminal carbon, as depicted, or the attachment may be to the penultimate carbon giving the primary alcohol.

Support materials bearing amino groups may be coupled to compounds of Formula II wherein R is carboxy or carboxysuccinimide or to compounds of Formula III, all reactions being carried out by procedures known in the art. For example, in coupling an amino bearing support material to an aminocarboxylic acid of Formula II, an excess of the acid is combined with the support material in a protic solvent, such as, aqueous dimethylformamide, at a pH of about 4.7 in the presence of a 10 to 100 fold molar excess of a water soluble carbodiimide, such as, N-ethyl-N'-(3-dimethylaminopropyl)carbodiimide HCl. See Formula C. In coupling a succinimide derivative of Formula II with an amino bearing support material a 10-fold molar excess of succinimide derivative is added to the support material in an aqueous buffer system, such as, 0.2M triethylamine acetate or phosphate or pyrophosphate at a pH ranging from 7 to 9.5 and the mixture is stirred at room temperature for about 12 to 24 hours. See Formula C. The compounds of Formula III are coupled to support materials bearing amino functions by combining an excess of the Formula III compound with the support material in a 50% aqueous solution of dioxane at a pH of about 11. The reaction is allowed to proceed for about 12 hours at 50° C. or up to 24 hours at room temperature. See Formula B wherein $R_4$ is NH. Under essentially the same conditions support materials bearing a halogen function are coupled to compounds of Formula II. See Formula D.

Support materials bearing carboxy groups may be coupled to compounds of Formula II by the same general carbodiimide activation procedure described hereinabove for coupling amino bearing support materials to the aminocarboxylic acids of Formula II. See Formula E. Support materials bearing succinimide groups may be coupled to compounds of Formula II by the same general procedures described hereinabove for coupling amino bearing support materials with compounds of Formula II wherein R is a carboxysuccinimide group. See Formula E. Also support materials bearing functional epoxy groups are coupled to compounds of Formula II by the same general procedure as described for coupling amino bearing support materials to compounds of Formula III. See Formula F.

When compounds of Formula III are coupled to appropriate support materials, i.e., those bearing either functional amines, hydroxyl or sulfhydryl groups, under conditions of lower pH than described above, the epoxide ring opens in such a manner as to have a support material-spacer arm unit having a primary alcohol as depicted in Formula G wherein $R_4$ is oxygen, sulfur or —NH— and m is an integer of 2 to 6. Similarly reaction of compounds of Formula II with support materials bearing an epoxy function under conditions of lower pH results in support material-spacer arm units as depicted in Formula H wherein Q and R have the meanings defined in Formula II.

The thus formed units depicted in Formulas A to H are reacted with the ligands of Formula IV by known means as generally described above. The compound units of Formulas A, C–F and G containing a terminal amine group are reacted with compounds of Formula IV wherein X is COOH and the compounds of Formulas A, D–F and H containing a terminal carboxy are reacted with compounds of Formula IV wherein X is NH₂ or with 2-(2,4-dichloro-5-phenylphenoxy)ethylamine or 2-(2,3-dichloro-6-phenylphenoxy)ethylamine by the standard carbodiimide activation coupling reaction described above. The compound units of A, D–F and H containing a terminal carboxysuccinimide group are reacted with a ligand of Formula IV wherein X is NH₂ or with 2-(2,4-dichloro-5-phenylphenoxy)ethylamine or 2-(2,3-dichloro-6-phenylphenoxy)ethylamine by combining the appropriate compound unit with a 10-fold molar excess of ligand in an aqueous buffer system, e.g., 0.2M triethylamine acetate or a phosphate or pyrophosphate buffer at a pH of about 7 to 9.5 at about 25° C. with stirring for about 12 to 24 hours. The compounds of Formulas B and G are reacted with the ligands of Formula IV wherein X is NH₂, sulfhydryl or hydroxyl or with 2-(2,4-dichloro-5-phenylphenoxy)ethylamine or 2-(2,3-dichloro-6-phenylphenoxy)ethylamine by combining the ligand and an excess of the epoxide compound of Formula B or G in, for example, a 50 percent aqueous dioxane solution at a pH of about 11 and allowing the reaction to proceed at about 50° C. for about 12 hours. In a similar manner the compounds of Formulas A, C–F and H containing a terminal amine group and the ligands of Formula IV wherein X is epoxy or halo or

are coupled and when X is halo-containing it may be desirable to run the reaction at about 25° C. for up to about 24 hours.

The thus formed affinity resins may be depicted as shown in Formulas J and K. In Formula J, O~ represents the support material which has attached thereto one of the functional linkages depicted in the left-hand bracket which linkage is attached to one end of the group Q which is defined as in Formula II. The other end of the group Q is attached to one of the functional linkages in the right-hand bracket which linkage is attached to L. The group L in Formulas J and K is the same as the compounds of Formula IV only the X group of the Formula IV compounds is removed, i.e., L is

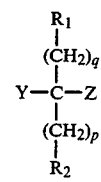

wherein Y, Z, q, p, $R_1$ and $R_2$ are as defined in Formula IV, or when the functional linkage in the right-hand bracket is other than

L may be 2-(2,4-dichloro-6-phenylphenoxy)ethanyl or 2-(2,3-dichloro-6-phenylphenoxy)ethanyl.

In the affinity resins depicted by Formula K the support material O~ is attached to one of the functional linkages in the bracket which linkage is attached to the remainder of the molecule via —CH₂—. In Formula K, m is the integer 2 to 6, each of $R_4$ and $R_5$ is sulfur, oxygen or NH and L has the meaning defined in Formula J with the proviso that when L is 2-(2,4-dichloro-6-phenylphenoxy)ethanyl or 2-(2,3-dichloro-6-phenylphenoxy)ethanyl, $R_5$ is NH.

The affinity resins of Formula V are prepared by reacting a compound of Formula IV wherein Y contains at least 3 carbons in a straight chain relationship with suitable support materials utilizing the same chemical procedures described hereinabove for preparing the affinity resins depicted in Formulas J and K. The resulting products are illustrated by Formula M wherein $R_6$ is NH, sulfur or oxygen and L represents the compounds of Formula IV except the X group is removed and Y contains at least three straight chain carbon atoms.

Most of the compounds of general Formula IV are known in the art and are either commercially available or are prepared by generally known methods, and it is apparent that certain of the compounds of Formula IV can be used to prepare other compounds of said formula.

Compounds wherein Y is methylene and both p and q are zero may be prepared by alkylating for example an appropriately substituted diphenylacetonitrile with an alkyl$C_{1-4}$ halide in a solution of dimethylformamide and sodium hydride then reduced with, e.g., lithium aluminum hydride to give the correspondingly substituted 2-alkyl-2,2-diphenylethaneamine. The amines may also be obtained by converting the alkylated nitrile to the corresponding amide by treatment with sulfuric acid with subsequent reduction of the amide using, e.g., borone. Or, the alkylated nitrile can be reduced with, e.g., diisobutylaluminum hydride to give the corresponding carboxaldehyde derivative which may be converted to the corresponding epoxide using a trimethylsulfonium halide. Also, the nitrile may be converted to the corresponding carboxylic acid by treatment with aqueous base and treatment of the acid with thionyl halide, e.g., thionyl chloride, gives the corresponding acid halide. Or the acid may be treated with a lower alcohol such as ethanol under mildly acidic conditions to give the lower alkyl ester which in turn is reduced with, e.g., lithium aluminum hydride to give the corresponding alcohol. The thus obtained alcohol may be treated with $P_2S_5$ to give the corresponding thiol, or, the alcohol thus obtained may be treated with a thionyl halide such as thionyl chloride or with phosphonyl chloride/phosphorus pentachloride in carbontetrahalide such as carbon tetrachloride and triphenylphosphine to give the corresponding halide derivative. The resultant halide may be treated with potassium cyanide to give the correspondingly substituted 2-alkyl-2,2-diphenylethanonitrile which may be treated as described hereinabove to give compounds of Formula IV wherein Y is ethylene and by following this procedure all of the compounds wherein Y is an alkylene chain of 1 to 4 carbon atoms and both p and q are zero are prepared. Compounds of Formual IV wherein p and q are other than zero can be prepared in a similar manner from the appropriate nitrile which may be prepared by known procedures. For example, the nitrile may be obtained by treating an appropriately substituted ketone derivative, e.g., benzyl phenyl ketone, phenethyl phenyl ketone or benzophenone with an alkyl Grignard to give the corresponding alkylated alcohol which can be converted to the corresponding thiol using $P_2S_5$ or to the corresponding halide using in carbon tetrahalide, e.g., tetrachloride and triphenylphosphine with alcohol. The halide can then be used to obtain the nitrile by treating with potassium cyanide and dimethylsulfoxide which can be used to obtain the other compounds of Formula IV as described above. However, in utilizing such a nitrile to give the amine derivative it may be more desirable to first hydrolyze the nitrile to the amide using sulfuric acid then treat the amide with $Br_2$/NaOH under the conditions of a Hofman Reaction [Ber. 14, 2775 (1881)] to give the amine.

The thus formed novel affinity resins specifically bind bacterial luciferase, and in particular luciferases from samples of lysed *Vibrio fischeri*, and *Photobacterium phosphoreum* and *Vibro harveyi* bind to and elute from the affinity resins resulting in high yields of pure enzyme. The means by which this binding is believed to occur is discussed in Biochemistry 1981, 20, 5524–5528. See also Biophysical Journal 33, part 2, 255 (1981). Another important aspect of the present invention is the fact that the amount of time required to recover these high yields of homogeneous enzyme is reduced quite significantly from previously known procedures. Another marked advantage of the presently claimed method is that it can be scaled up or down with relative ease to accommodate recovery of large or small quantities of enzyme as needed. Additionally, the novel affinity resins of the present invention may be used repeatedly for isolation of enzyme. That is, after the affinity resin has been used to isolate bacterial luciferase, it may be washed with, e.g., a 1:1 mixture of 8M urea and 50% ethanol containing 0.08M phosphate, then reequilibrated with anionic buffer and used again for isolation of enzyme.

Bacterial luciferase is known to be useful in the assay of proteases as the luciferase enzyme is highly susceptible to inactivation by a wide variety of proteases such as, for example, trypsin, elastase, chymotrypsin, plasminogen and collagenase, several of which are known to be involved or are implicated in certain disease conditions, such as, autoimmune diseases, e.g., rheumatoid arthritis, in certain types of carcinoma, emphysema and in peridontal diseases. Therefore, the use of bacterial luciferase in an enzyme assay system provides a useful means of detecting protease activity which may lead to the detection of certain disease conditions. Aside from its utility in assaying proteinases, luciferase can also be used in a coupled enzyme assay system for detecting the levels of nucleotides like NADH, NADPH, and FMN in serum or tissue samples. See P. E. Stanley (1978) Meth. Enzymol, 57, 215–223, or for detecting the presence of other enzymes utilizing these nucleotides, see P. E. Stanley (1978) Meth. Enzymol. 57, 181–189.

When isolating the bacterial luciferase enzyme by means of the present invention, in general the novel affinity resin is equilibrated with an anionic buffer solution and is then contacted with a sufficient amount of enzyme sample suspended in the same anionic buffer to saturate the binding sites on the affinity resin, after which the affinity resin is washed with additional anionic buffer to remove materials contained in the enzyme sample which do not bind and subsequently the affinity resin is eluted or washed with a cationic or neutral buffer to release the bound enzyme. Thus the enzyme may be isolated by any means which will permit contact of the sample containing the bacterial luciferase to be isolated with the equilibrated affinity resin in an appropriate anionic buffer with subsequent washing of the affinity resin containing the bound enzyme followed by treatment with an appropriate cationic or neutral buffer. Thus the enzyme may be isolated using batch isolation techniques or column chromatographic techniques, the latter of which is preferred. It is important, particularly when column chromatographic techniques are employed, that the affinity resin be saturated with the enzyme sample. When using batch separation methods binding to the affinity resin is measured by disappearance of enzyme activity from the suspending solution, and following the removal of unbound protein from the mixture, release and recovery of the enzyme by treatment with cationic buffer is measured by the increase in enzyme activity in the supernatant. Similarly when using column chromatography, saturation of the affinity resin is measured by the appearance of enzyme activity in the eluate fractions collected.

It has been determined that the enzyme binding capacity of the affinity resin is about 5 to 25 mg of bacterial luciferase per milliliter (ml) of suspended affinity resin depending upon the number of affinity ligand molecules attached to the support resin. When using column chromatography the capacity of column containing the equilibrated affinity resin is about 5 to 25 mg of bacterial luciferase per ml of column volume.

The enzyme may be isolated at various temperatures although it is convenient and practical to perform the isolation in a cold room, e.g., about 4° C. Of course, the separation could be performed at significantly higher or lower temperatures, however, it may become necessary to add to the medium agents which will retard bacterial growth and, of course at very low temperatures, means to prevent freezing of the medium may be required.

It is known that bacterial luciferase has an anionic binding site. See, e.g., Holzman and Baldwin, Biochem. Biophys. Res. Comm. 94, No. 4, 1199 (1980) and Proc. Natl. Acad. Sci. 77, No. 11, 6262 (1980). Therefore an anionic buffer system is employed in the present invention to facilitate binding of the enzyme to the affinity resin. Generally the enzyme affinity for the novel resin is enhanced with increasing anionic strength of the buffer. The anionic buffer has a pH ranging from about 6.5 to 9.5, and an overall ionic strength of about 0.01M to about 2M. Preferably the pH of the buffer is about 8 to 8.5 and the ionic strength is about 0.2 to 1M. The anionic buffer consists of an aqueous solution of an alkali metal salt, e.g., potassium or sodium, of phosphate, preferably, although salts of citrate, pyrophosphate, arsenate, sulfate or equivalents thereof may be used or mixtures of these salts may be used. The anionic buffer also contains a thiol containing reducing agent at a concentration of about 1mM. Suitable reducing agents include dithioerythritol, dithiothrietol, mercaptoethanol, cysteamine, cysteine, thiodiglycol, or glutathione.

As indicated hereinabove the anionic buffer is used to equilibrate the affinity resin, and is also used to suspend the sample containing the bacterial luciferase to be isolated and is used to wash the unbound materials away from the affinity resin once it becomes saturated with enzyme.

The cationic or neutral buffer employed in the present invention reduces the affinity of the enzyme for the novel resin. Generally any organic amine containing buffer may be used, such as commercially available TRIS, 2-amino-2-hydroxymethyl-2,4-propanediol; HEPES, 4-(2-hydroxyethyl)-1-piperazineethanesulfonic acid; TES, 2-[[tris-(hydroxymethyl)methyl]amino]ethanesulfonic acid, or ethanolamine alone or in combination with other amine buffers. Ethanolamine is particularly useful in the isolation of *Vibrio harveyi* luciferase. The ionic strength of the buffer should be relatively low and not exceed about 1M. The pH should be maintained at about 6.5 to 9.5. The cationic buffer system also contains a thiol containing reducing agent at a concentration of about 1mM. Suitable reducing agents include those enumerated above in conjunction with the anionic buffer system.

Typically in practicing the invention an affinity resin as described herein is suspended in an anionic buffer as described above and poured into a column. The resin is equilibrated with the anionic buffer. The sample containing the bacterial luciferase to be isolated is suspended in the anionic buffer and poured onto the column. The column size is determined by the amount of enzyme present in the sample to be isolated which is determined by the enzyme activity of the sample. Once the affinity resin is saturated the column is washed with anionic buffer to remove unbound material, then the column is eluted using cationic or neutral buffer above described. The elution step generally requires about 4 to 8 column volumes of buffer. Fractions are collected and an elution curve is generated. The yield of enzyme recovered is measured by the enzyme activity recovered.

If all fractions collected are pooled, essentially 100 percent of the enzyme is recovered. We have found that when 90% of the initial total of enzyme activity is recovered the protein or enzyme is about 50% pure. Of course one may select only those fractions having highest enzyme activity to increase the purity of recovered protein. When 75 percent of the initial total activity is recovered the purity of the enzyme is about 65% and when 50% of the initial total activity is recovered the enzyme is about 90% pure.

The following examples further illustrate the invention.

EXAMPLE 1

The following illustrates the preparation of a typical affinity resin as depicted by Formula K wherein the bracketed functional group is

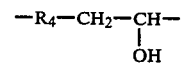

and $R_4$ is oxygen, m is 4, $R_5$ is NH and L is 2,2-diphenylpropanyl.

To about 50 ml of Sepharose 6B is added 50 ml of 1,4-diglycidyl ether, i.e., 1,4-bis(2,3-epoxypropoxy)butane, 50 ml of 0.6M sodium hydroxide and 100 mg of sodium borohydride. The slurry thus formed is mixed by rotation for about 8 hours at about 25° C., then poured onto a sintered glass funnel and washed to neutrality with distilled water and suction dried. This procedure is generally described by Sunderberg and Porath, J. Chrom. 90, 87 (1974).

The thus formed epoxy activated Sepharose is reacted with 2,2-diphenylpropylamine. For each gram of epoxy activated Sepharose employed 100 mg of 2,2-diphenylpropylamine is used. The alkylamine is dissolved in 50% dioxane/50% 0.20M carbonate buffer pH 10.5 (1 ml of the liquid in dioxane buffer per gram of Sepharose). The solution pH is maintained at pH 10.5. The activated Sepharose is then added and the flask containing the thus formed slurry is placed in a water bath at −60° and rotated for 24 hours. During the first 12 hours the pH of the slurry is checked at three hour intervals, then again at 18 hours and 24 hours and adjusted to pH 10.5 if necessary. The immobilized inhibitor, that is, the thus formed affinity resin is then carefully washed out of the flask and into a coarse pore sintered glass funnel attached to a vacuum filtration system. For each gram of the suction-dried Sepharose used initially, the affinity resin is washed sequentially with the following mixtures: 6 ml of 1:1 dioxane/water, 6 ml of 1:1 dioxane/0.20M phosphate pH 7.0, and 12 ml of 95% ethanol. The affinity resin may be used directly or may be stored in 50% ethanol/water. Generally, 1–2 μmole of ligand is attached per milliliter of resin by this procedure.

To pack a column, a gel slurry is prepared by adding an equal volume of application, buffer, i.e., anionic buffer, and swirling gently. The slurry is poured into the column. The packed column is equilibrated by washing with about 4 column volumes of anionic buffer before beginning sample application.

EXAMPLE 2

The following describes the preparation of an affinity resin as depicted by Formula J wherein the left-hand bracketed functional group is

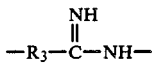

and $R_3$ is oxygen: the right-hand bracketed functional group is

and L is 2,2-diphenylpropanyl.

A 5 ml solution of cyanogen bromide (prepared at 100 mg/ml) in dimethylformamide is added to 100 ml of Sepharose 6B which had been equilibrated in 100 ml of 2M sodium carbonate. During cyanogen bromide activation, which requires about 10 minutes and is carried out at about 25° C., the gel is held in a sintered-glass funnel and is gently agitated by bubbling nitrogen through the fritted glass disk of the funnel. The activation procedure is outlined by March, et al., (1974) Anal. Biochem. 60, 149. Following cyanogen bromide activation the gel is washed with water to neutrality, then resuspended in 200 ml, 0.10M aqueous solution of 1,6-hexanediamine at pH 9.5. The mixture is allowed to gently stir at 4° C. for 12 hours, then is washed to neutrality with water on the sintered glass funnel.

To 10 ml of the thus formed resin or gel bead spacer arm unit is added 100 mg of N-ethyl-N'-(3-dimethylaminopropyl)carbodiimide HCl and 200 mg of 2,2-diphenylpropionic acid in 20 ml of 50% dioxane/water, pH 6.0. Upon completion of the addition the pH is adjusted 6.0 and the mixture is stirred using a rotary stirring apparatus. After about 2 hours the pH tended to decrease and was adjusted to 6 as needed. After the initial drop in pH the mixture is stirred for 24 hours at about 25° C. The gel is washed to neutrality with water on a vacuum filter to give the novel affinity resin.

The foregoing carbodiimide coupling typically results in substitution in the range of 1 to 2 μmoles per ml of resin.

EXAMPLE 3

The following illustrates the method of isolating bacterial luciferase from a sample as herein claimed. The enzyme source is *Vibrio harveyi*.

A cell lysate is prepared from 100 gm of frozen cell paste by the osmotic lysis technique described by Hastings, et al., Meth. Enzymol. 57, 135 (1978). Ammonium sulfate is added to the lysate (1100 ml) to 40% of saturation and centrifuged at 8000 RPM for 1–1.5 hours in a Sorvall GSA rotor at 4° C. The lysate is allowed to equilibrate with the ammonium sulfate for about 30 minutes prior to centrifugation. The supernatant (1100 ml) is collected and more ammonium sulfate added to 80% saturation. The pellets from the first centrifugation, containing cell debris and precipitated protein, are discarded. The supernatant with ammonium sulfate at 80% saturation is centrifuged at 8000 RPM, 4° C., for one hour in a GSA rotor. The pellets are collected and transferred to dialysis tubing and dialyzed at 4° C. into the application or anionic buffer. Transfer of the pellets into the dialysis tubing, preparation of the buffer for dialysis, etc., requires about 2 hours. The crude luciferase sample is dialyzed versus 3 changes of 1 liter each for a total of about 12 hours at 4° C. The sample is then centrifuged at 15,000 RPM in an SS-34 rotor for 30 minutes at 4° C. The total volume of supernatant is 245 ml. Half of the clear solution (120 ml) is then applied to a 15 ml column of the affinity matrix equilibrated in the application buffer. The application flowrate is about 40 ml/hr. By assays of eluate from the column for luciferase activity, it is determined that the column is saturated with luciferase by this amount of activity. The column is then washed with 4 column volumes (60 ml) of application buffer at a flowrate of about 15 ml/hr to elute unbound or weakly bound protein. The column is then eluted with 4 column volumes of elution buffer; 1 ml fractions are collected and assayed for luciferase activity. Fractions containing about 90% of the luciferase activity are pooled, concentrated by ammonium sulfate precipitation (80% of saturation), dialyzed and subjected to chromatography on aminohexyl Sepharose as described by Hastings, et al, ibid.

Purity of the enzyme is estimated by Coomassie blue staining of protein bands resolved by sodium dodecylsulfate gel electrophoresis in polyacrylamide as described by Laemmli, Nature 227, 680 (1970). Pure luciferase (>95%) has a specific activity of about 30,000 (±10%) light units per mg of protein when assayed by the standard flavin injection assay described in detail by Hastings, et al. One light unit is $1.06 \times 10^{10}$ quanta/sec based on the liquid light standard of Hastings and Weber, J. Opt. Soc. Am. 53, 1410 (1963).

The following Table summarizes the foregoing and the results obtained.

Following the same general procedure as described in Example 3 only using from 2 to 5 grams of cell paste prepared from *Vibrio* (photobacterium) *fischeri* or *Photobacterium phosphoreum* and adjusting the volumes of reagents appropriately essentially all the applied affinity (>95%) is recovered with a purity >95%.

TABLE I

Purification Table for *V. harveyi* Luciferase

| Step | Vol. (ml) | $A_{280}$ | Total $A_{280}$ | Activity* (L.U./ml) | Total Activity (L.U.) | Specific Activity L.U./$A_{280}$ | Fold Purification (Previous Step) | Time/Step | % Yield (Initial Total Act.) |
|---|---|---|---|---|---|---|---|---|---|
| Osmotic Lysis | 1100 | 28.0 | 30800 | 5300 | $5.85 \times 10^6$ | 189 | — | — | — |
| 40% Ammonium sulfate supernatant | 1100 | — | — | 5300 | $5.85 \times 10^6$ | — | — | ~1 hour from thawed cells | — |
| 80% AMS PPT | | | | | | | | ~2 hour centrifugation @ 8000 RPM GSA Rotor, 4° C. 1-3 hour cent., 4° C. 8000 RPM GSA Rotor | |
| Dialysis into affinity column application buffer | 245 | 42.5 | 10412 | 23900 | $5.85 \times 10^6$ | 562 | 2.98 | 12 hours, 3 changes of buffer | 100% |
| Affinity column*** pool Applied $2.66 \times 10^6$ Tot. L.U. | 24 | 6.1 | 146 | 95000 | $2.28 \times 10^6$ | 15600 | 27.8 | Total run time ~12 hours | 88% |
| AH—Sepharose column pool: Applied 60 ml** $A_{280}$ = 3.85 in 5.0 mM $PO_4$, pH 7.0, 0.50 mM DTE ~$4.9 \times 10^6$ T.L.U. | 76.6 | 1.58 | 121 | 50160 | $3.84 \times 10^6$ | 32000 | 2.05 | Total run time ~16 hours | 66% |

*1 L.U. = $1.06 \times 10^{10}$ hv/sec
**Two affinity column preps from the original lysis
***Column volume = 15 ml, 2 cm diameter; note only half of total sample is applied.

Affinity column application buffer:
0.10 M PO (Na/K—Phosphate), pH 8.5.
0.50 mM DTE
0.50 M KCl
0.50 M NaCl Affinity column elution buffer:
0.025 M ethanolamine, 5 mM TRIS, pH 9.1.
0.05 mM DTE Note: Both affinity column and AH—Seph. column are pumped.

CHART A

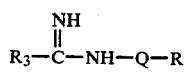 Formula A

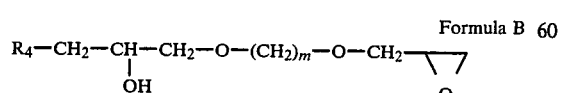 Formula B

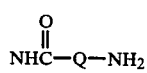 Formula C

NH—Q—R  Formula D

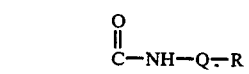 Formula E

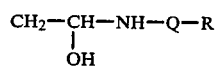 Formula F

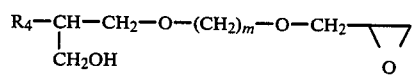 Formula G

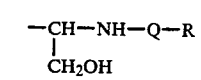 Formula H

CHART B
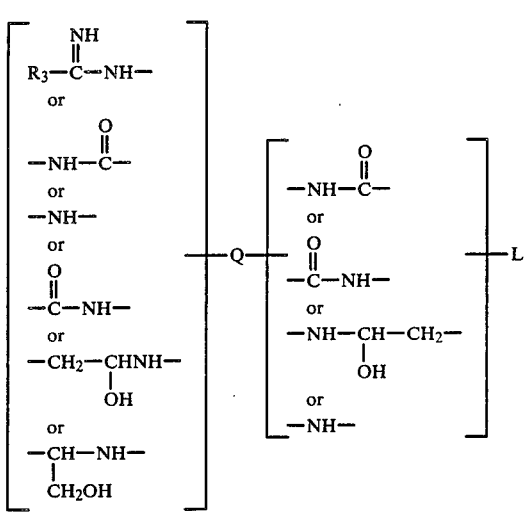
Formula J
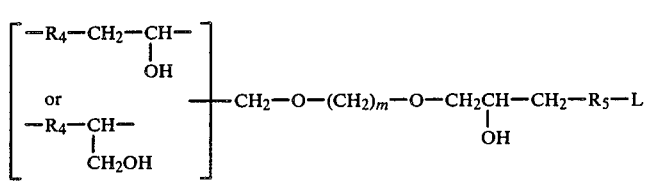
Formula K
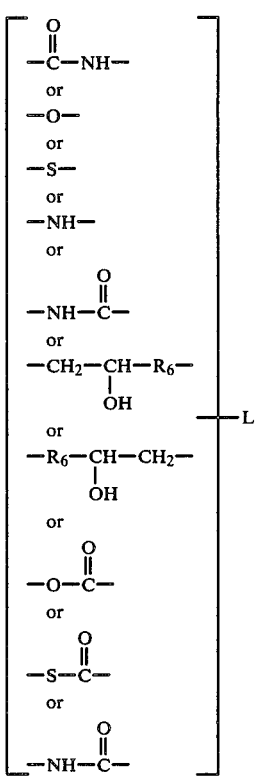
Formula M
We claim:
1. An affinity resin as described in the following Formulas J and K which comprises a support material, a spacer arm, and a ligand wherein represents the support material; $R_3$ is oxygen or sulfur; each of $R_4$ and $R_5$ is sulfur, oxygen, or —NH—; m is an integer of 2 to 6; Q is a straight or branched alkylene moiety having from 2 to 8 carbon atoms; L is

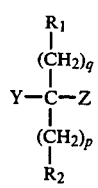

wherein Y is a bond or an alkylene chain of 1 to 4 carbon atoms, one or 2 carbon atoms of which may be branched; Z is hydrogen or a straight or branched alkyl group having from 1 to 4 carbon atoms; q is zero or one; p is zero, one or 2; $R_1$ is hydrogen, phenyl or phenyl substituted with one or 2 substituents selected from halogen, trihalomethyl, a straight or branched alkoxy group having from 1 to 4 carbon atoms or a straight or branched alkyl group having from 1 to 4 carbon atoms; and $R_2$ is ortho, meta or para-biphenylyl, phenyl, or phenyl substituted with one or 2 substituents selected from halogen, trihalomethyl, a straight or branched alkoxy group having from 1 to 4 carbon atoms or a straight or branched alkyl group having from 1 to 4 carbon atoms with the provisos that: (a) when $R_2$ is biphenylyl, each of p and q is zero and $R_1$ is hydrogen; (b) when p is 2, q is zero; and (c) when $R_2$ is other than biphenylyl, $R_1$ is other than hydrogen, or when the functional linkage in the right hand bracket is other than

L is 2-(2,4-dichloro-6-phenylphenoxy)ethanyl or 2-(2,3-dichloro-6-phenylphenoxy)ethanyl:

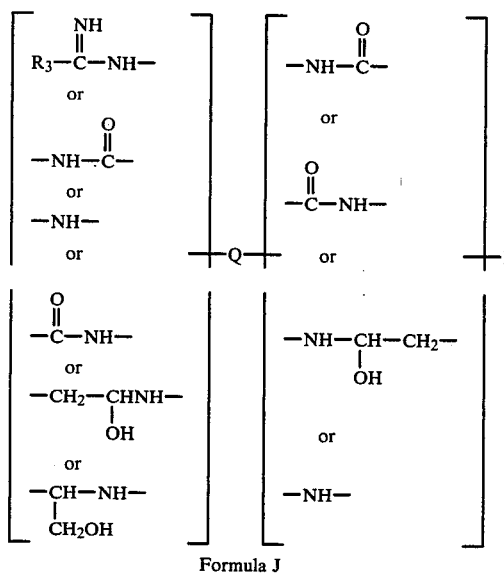

Formula J

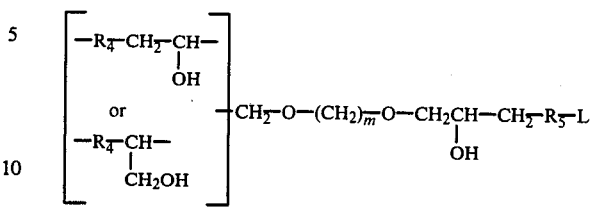

Formula K

2. An affinity resin as described in the following Formula M which comprises a support material and a ligand wherein represents the support material; $R_6$ is —NH—, sulfur, or oxygen; L is

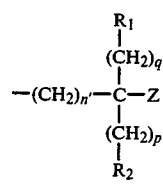

wherein n' is 3 or 4; Z is hydrogen or a straight or branched alkyl group having from 1 to 4 carbon atoms; q is zero or one; p is zero, one or 2; $R_1$ is hydrogen, phenyl or phenyl substituted with one or 2 substituents selected from halogen, trihalomethyl, a straight or branched alkoxy group having from 1 to 4 carbon atoms or a straight or branched alkyl group having from 1 to 4 carbon atoms; and $R_2$ is ortho, meta or para-biphenylyl, phenyl, or phenyl substituted with one or 2 substituents selected from halogen, trihalomethyl, a straight or branched alkoxy group having from one to 4 carbon atoms or a straight or branched alkyl group having from 1 to 4 carbon atoms with the provisos that: (a) when $R_2$ is biphenylyl, each of p and q is zero and $R_1$ is hydrogen; (b) when p is 2, q is zero; and (c) when $R_2$ is other than biphenylyl, $R_1$ is other than hydrogen:

Formula M

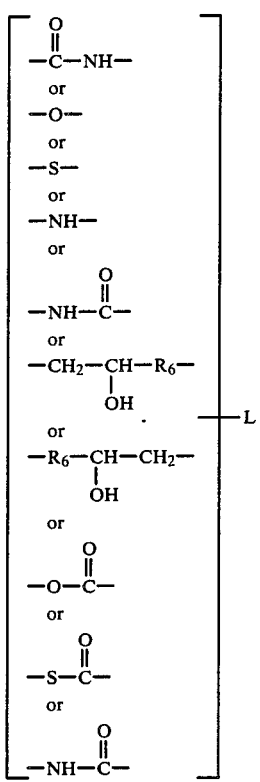

3. An affinity resin of claim 2 which specifically binds bacterial luciferase.

4. An affinity resin of claim 1 or 2 which specifically binds bacterial luciferase.

5. An affinity resin of claim 1 wherein the moiety L is 2-(2,3-dichloro-6-phenylphenoxy)ethanyl or has the structure:

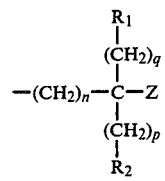

wherein n is zero to 4; $R_1$ is hydrogen or phenyl; $R_2$ is ortho-, meta- or para-biphenylyl or phenyl; q is zero or one; p is zero, one or two; and Z is hydrogen or a straight or branched alkyl group having from 1 to 4 carbon atoms; with the provisos that (a) when $R_2$ is biphenylyl each of p and q is zero and $R_1$ is hydrogen, (b) when p is two, q is zero, and (c) when $R_2$ is other than biphenylyl $R_1$ is other than hydrogen.

6. An affinity resin of claim 5 wherein n is 0 to 3; Z is hydrogen, methyl or ethyl; and each of $R_1$ and $R_2$ is phenyl.

7. An affinity resin of claim 6 wherein each of p and q is zero, and Z is hydrogen or methyl.

8. An affinity resin of claim 5 wherein L is 2-(2,3-dichloro-6-phenylphenoxy)ethanyl.

9. An affinity resin of claim 2 wherein the L moiety has the structure

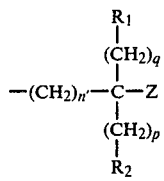

wherein n' is 3 or 4; $R_1$ is hydrogen or phenyl; $R_2$ is ortho-, meta- or para-biphenylyl or phenyl; q is zero or one; p is zero, one or two; and Z is hydrogen or a straight or branched alkyl group having from 1 to 4 carbon atoms; with the provisos that (a) when $R_2$ is biphenylyl each of p and q is zero and $R_1$ is hydrogen, (b) when p is two, q is zero, and (c) when $R_2$ is other than biphenylyl $R_1$ is other than hydrogen.

10. An affinity resin of claim 9 wherein Z is hydrogen, methyl or ethyl and each of $R_1$ and $R_2$ is phenyl.

11. An affinity resin of claim 10 wherein each of p and q is zero and Z is hydroxy or methyl.

12. An affinity resin of claim 9 wherein L is 2-(2,3-dichloro-6-phenylphenoxy)ethanyl.

* * * * *

UNITED STATES PATENT OFFICE
CERTIFICATE OF CORRECTION

Patent No. 4,548,994    Dated October 22, 1985

Inventor(s) Thomas O. Baldwin and Thomas F. Holzman

It is certified that error appears in the above-identified patent and that said Letters Patent are hereby corrected as shown below:

-- [73] Assignee: Board of Trustees of The University of Illinois, Urbana, Ill. -- instead of the assignee shown on the printed patent.

Column 15, line 68, "a ligand wherein" should read -- a ligand wherein  --.

Column 17, Formula J, leftmost side:

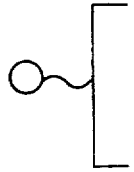

Column 18, Formula K, leftmost side:

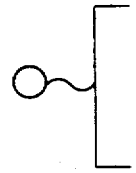

Column 18, Claim 2, lines 15-20:

UNITED STATES PATENT OFFICE
CERTIFICATE OF CORRECTION

Patent No.  4,548,994     Dated  October 22, 1985

Inventor(s)  Thomas O. Baldwin and Thomas F. Holzman

It is certified that error appears in the above-identified patent and that said Letters Patent are hereby corrected as shown below:

Column 19, Formula M, leftmost side:

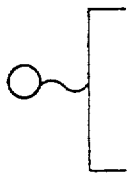

Signed and Sealed this

Twenty-fifth Day of March 1986

[SEAL]

Attest:

Attesting Officer

DONALD J. QUIGG

Commissioner of Patents and Trademarks